United States Patent
Sasaki et al.

(10) Patent No.: US 6,962,747 B1
(45) Date of Patent: Nov. 8, 2005

(54) SELF-ASSEMBLED LIPID BILAYER MATERIALS

(75) Inventors: Darryl Y. Sasaki, Albuquerque, NM (US); Tina A. Waggoner, Rio Rancho, NM (US); Julie A. Last, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 448 days.

(21) Appl. No.: 10/041,846

(22) Filed: Oct. 23, 2001

(51) Int. Cl.$^7$ .............................. B32B 3/26; B32B 5/02; B32B 7/10; B32B 33/00; A61K 9/127

(52) U.S. Cl. ...................... 428/332; 428/220; 428/336; 424/1.21; 424/450; 436/829

(58) Field of Search .............................. 428/212, 213, 428/220, 332, 333, 336, 338, 373, 380, 397, 428/409, 910, 411.1; 257/E51.045; 424/1.21, 424/450; 436/829; 427/213.3, 213.31, 213, 427/36; 264/4.3, 4.6, 4.32, 4.33

(56) References Cited

U.S. PATENT DOCUMENTS

| | | | |
|---|---|---|---|
| 5,837,202 A | 11/1998 | Arnold et al. | |
| 5,925,375 A * | 7/1999 | Lenk et al. | 424/450 |
| 6,284,267 B1 * | 9/2001 | Aneja | 424/450 |
| 6,358,523 B1 * | 3/2002 | Safinya et al. | 424/450 |
| 6,537,575 B1 * | 3/2003 | Firestone et al. | 424/484 |

OTHER PUBLICATIONS

Waggoner, et al., "Self-Assembled Columns of Stacked Lipid Bilayers Mediated by Metal Ion Recognition," *J. Am. Chem. Soc.*, 2001, 123, 496-497 (no month).

Ringsdorf, et al., "Molecular Architecture and Function of Polymeric Oriented Systems: Models for the Study of Organization, Surface Recognition, and Dynamics of Biomembranes" *Angew. Chem. Int. Ed. Engl.*; 27, 113-158, Jan. 1988.

Alberts, et al., "Molecular Biology of The Cell, 3rd ed." Garland Publishing, 1994, pp. 127-128, 276, 576, 1142-1143 (no month).

Radler, et al., "Structure of DNA-Cationic Liposome Complexes: DNA Intercalation in Multilameller Membranes in Distinct Interhelical Packing Regimes," *SCIENCE*, vol. 275, Feb. 7, 1997, 810-813 (www.sciencemag.org).

Wong, et al., "Hierarchical Self-Assembly of F-Actin and Cationic Lipid Complexes: Stacked Three-Layer Tubule Networks," *SCIENCE*, vol. 288, Jun. 16, 2000, 2035-2039 (www.sciencemag.org).

Constable, et al., "Reversible metal-directed assembly of clusters and vesicles" *Chem. Commun.*, 1999, 1483-1484 (no month).

Chiruvolu, et al., "Higher Order Self-Assembly of Vesicles by Site-Specific Binding," *SCIENCE*, vol. 264, Jun. 17, 1994, 1753-1756 (www.sciencemag.org).

(Continued)

*Primary Examiner*—Michael E. Lavilla
(74) *Attorney, Agent, or Firm*—Elmer A. Klavotter

(57) ABSTRACT

The present invention is a self-assembling material comprised of stacks of lipid bilayers formed in a columnar structure, where the assembly process is mediated and regulated by chemical recognition events. The material, through the chemical recognition interactions, has a self-regulating system that corrects the radial size of the assembly creating a uniform diameter throughout most of the structure. The materials form and are stable in aqueous solution. These materials are useful as structural elements for the architecture of materials and components in nano-technology, efficient light harvesting systems for optical sensing, chemical processing centers, and drug delivery vehicles.

11 Claims, 2 Drawing Sheets

OTHER PUBLICATIONS

Sasaki, et al., "Optical detection of aqueous phase analytes via host-guest interaction on a lipid membrane surface," *SPIE-The International Society for Optical Engineering*, vol. 3606, Jan. 25-26, 1999, San Jose, CA, 46-54.

Sasaki, et al., "Metal-Induced Dispersion of Lipid Aggregates: A Simple, Selective, and Sensitive Flourescent Metal Ion Sensor," *Angew. Chem. Int. Ed. Engl.*, 1995, 34, No. 8, 905-907 (no month).

Sasaki and Padilla, "Dithioamide Metal Ion Receptors on Flourescent Lipid Bilayers for the Selective Optical Detection of Mercuric Ion," *Chem. Commun.*, 1998, 1581-1582 (no month).

Ng, et al., "Engineering Protein-Lipid Interactions: Targeting of Histidine-Tagged Proteins to Metal-Chelating Lipid Monolayers," *Langmuir*, vol. 11, No. 10, 1995, *Am. Chem. Soc.*, 4048-4055 (no month).

* cited by examiner

DSPC

PSIDA

SELF-ASSEMBLED LIPID BILAYER MATERIALS

This invention was made with Government support under Contract No. DE-AC04-94AL85000 awarded by the Department of Energy. The Government has certain rights in the invention.

BACKGROUND OF THE INVENTION

The present invention relates to a composition of lipid molecules and, more particularly, to a self-assembling material composed of lipid molecules induced, via chemical recognition, into a columnar structure with self-limiting dimensions and method of making.

Self-assembling materials are formed from single molecular or ionic components that have complementary interactions (both repulsive and attractive) to bring about the spontaneous formation of ordered supramolecular structures. In particular, liquid crystalline materials produce a myriad of supramolecular structures that can be tailored through their molecular geometry, functionality, and environmental conditions (e.g., salt concentration, temperature, and solvents). Lyotropic liquid crystalline materials, such as the lipid molecules, create vesicular, lamellar, and micellar structures in the aqueous phase (Ringsdorf, H.; Schlarb, B.; Venzmer, J. Angew. Chem. Int. Ed. Engl. 1988, 27, 113). The current and potential uses of such materials include models for cellular membranes and drug delivery vehicles. Block copolymers also can generate unique self-assembled structures in solvents, very similar to lipid molecules. However, their sheer size and chemical complexity can generate new structures and dimensions not previously observed with the lipids. Thermotropic liquid crystalline materials also form highly organized assemblies in two- and three-dimensions, forming discotic, lamellar, hexagonal, and cubic structures.

Although the liquid crystalline materials form highly ordered structures in both two- and three-dimensions, the materials do not exhibit any ability to self-regulate growth. Biological materials show numerous examples of structures that self-regulate growth, such as skeletal systems, tissue, virus particles, among others (Alberts, B.; Bray, D.; Lewis, J.; Raff, M.; Roberts, K.; Watson, J. D. *Molecular Biology of The Cell*; third ed.; Garland Publishing: New York, 1994). Known systems of lipid bilayer assemblies use ion complexation or molecular recognition at the membrane surface to form supramolecular aggregates with hierarchical structure. Examples include bilayer structures formed through bilayer-DNA (Radler, J. O.; Koltover, I.; Saldift, T.; Safinya, C. R. *Science* 1997, 275, 810) or bilayer-actin (Wong, G. C. L.; Tang, J. X.; Lin, A.; Li, Y.; Janmey, P. A.; Safinya, C. R. *Science* 2000, 288, 2035) complexation, metal ion coordination (Constable, E. C.; Meier, W.; Nardin, C.; Mundwiler, S. *Chem. Comm.* 1999, 1483), or biotin-streptavidin molecular recognition (Chiruvolu, S.; Walker, S.; Israelachvili, J.; Schmitt, F.-J.; Leckband, D.; Zasadzinski, J. A. *Science* 1994, 264, 1753). In none of these cases do the self-assembled material exhibit any ability to self-limit growth in any dimension.

Self-assembled materials with self-limiting dimensions can have use in a variety of applications for nanotechnology, which include scaffolding for device building, highly oriented structures for light harvesting, nano-scale chemical processing units, and unique drug delivery systems. Such materials are described in Waggoner et al. (Waggoner, T. A.; Last, J. A.; Kotula, P. G.; Sasaki, D. Y. *J. Am. Chem. Soc.* 2001, 123, 496–497).

BRIEF DESCRIPTIONS OF THE DRAWINGS

DETAILED DESCRIPTION OF THE INVENTION

Figure 1:
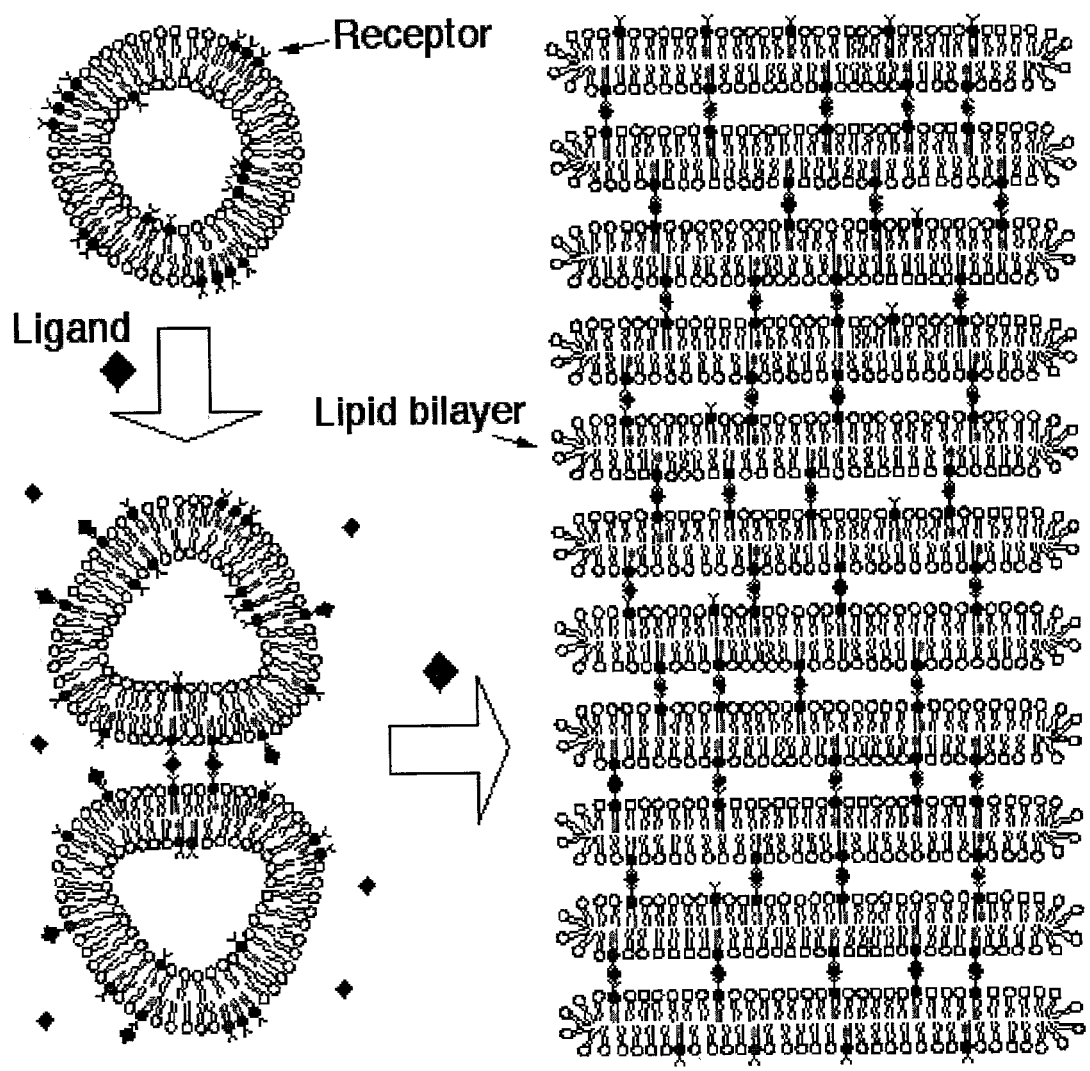
FIG. 1 shows a schematic illustration of the formation of columnar stacks of lipid bilayers induced through the chemical recognition interactions taking place between lipid bilayers.

The present invention is a self-assembling material composed of stacks of lipid bilayers formed in a columnar structure, where the assembly process is mediated and regulated by chemical recognition events. The material, through the chemical recognition interactions, has a self-regulating system that corrects the radial size of the assembly creating a columnar structure of approximately uniform diameter throughout most of the structure. The materials form and are stable in aqueous solution. The present invention also comprises the method of making these self-assembled lipid bilayer materials.

The present invention is the first known example of a self-assembled structure that is formed from a self-assembled material (lipid bilayer vesicles) with self-limiting dimensions dictated by chemical recognition at the membrane surface. These materials can be useful as structural elements for the architecture of materials and components in nanotechnology, efficient light harvesting systems for optical sensing, chemical processing centers, and drug delivery vehicles.

Columnar structures with defined sub-micron dimensions can offer excellent structural support to the fabrication of nano-scale devices. The developing field of nanotechnology depends on the development of materials as either permanent or temporary fixtures with nanometer scale size domains. As a permanent material, the present invention can provide a hierarchical structure of striated lipid bilayers self-contained in a rod-like shape. High molecular orientation within the bilayers can impart unique properties in the material, such as efficient light harvesting or high modulus strength, and the rod-like shape is a universally useful geometrical shape for structure building. As a temporary scaffold, the columnar structures can be formed in open, easily accessible areas as well as confined, difficult to access sites. Because the self-assembly is of small lipid molecules and the process is dictated by a chemical signal or ligand, the structures could be formed at any desired place and time. By fixing a bilayer down on a surface to act as a template, columns of stacked bilayers can be grown at any predetermined place with predetermined dimensions for use as support pillars. After the usage for the scaffold is complete, the bilayer stacks can be removed using a ligand scavenger to remove the chemical signal and the scaffold will self-disassemble.

As a light harvesting system, the present invention can provide efficient energy transfer throughout the structure. Nature uses bilayer stacks to efficiently harvest light in photorods and chloroplasts. Incorporated into the present invention, such light harvesting systems should enhance light-harvesting efficiency due to the high concentration of bilayers in a defined, asymmetric structure. This structure can be readily incorporated into various nanotechnology devices.

As a chemical processing center, the present invention can offer a unique environment to process chemical reactions in aqueous environments. The bilayer materials look very much and are compositionally similar to the endoplasmic reticulum (ER) in a biological cell, which is the cell's major chemical processing center. The present invention can, similarly, albeit synthetically, be functionalized with catalytic centers at or near the membrane surface. The high local concentration of catalytic centers in a highly oriented environment adjacent to a field of other bilayers functionalized with complementary catalytic sites can offer unique chemical processing centers in a compact and versatile structure. Incorporation of such a structure in a nano-device can provide an enhancement of performance of the device with unique chemistry, as well as physical structure for the architectural scaffold.

For drug delivery, the present invention can provide a new method to dispense drugs at specific sites with unique release rates. Drugs, either amphiphilic or hydrophobic, can be incorporated into the stacked bilayer structure. Functionalization of the bilayer surface with specific receptors can target the columnar structure to diseased cells or damaged tissue. Molecular recognition will deliver the material to a specific target site that can either have inherently low pH (e.g., in cancer cells) or specific surface functionalization (e.g., in diseased cells) that would sequester or release the chemical ligand used to assemble the bilayer stacks. The loss of ligand would affect disassembly of the bilayer stack and subsequent release of the drug.

The lipid bilayers are composed of lipid molecules, which are amphiphilic structures having both a hydrophilic and hydrophobic portion. The lipid components spontaneously form a lamellar structure in aqueous solution where the hydrophilic portions are oriented to the aqueous phase and the hydrophobic segments interact to form a hydrophobic core or layer. The lipid bilayers are formed in vesicular structures called liposomes and the bilayer material can be in either the two-dimensional liquid or solid phase.

Within the bilayer are receptor molecules that are tailored for specific interaction with a ligand. The ligand accommodates the binding of at least two receptors from different liposomes. Addition of the ligand causes two liposomes to adhere to each other through the receptor-ligand-receptor interaction. Subsequent multiple point binding interactions between the liposomes surface's, mediated by the chemical recognition events, causes the membranes to layer upon each other and flatten at the interface (see FIG. 1). The membrane flattening perturbs the membrane structure resulting in liposome lysis. Free ligands (such as $Cu^{2+}$) then permeate to the previously inaccessible interior of the liposome and initiates further adhesion between the bilayers of the same liposome. The initial stacked bilayers then, through the chemical recognition sites (adhesion points), act as a template to form bilayers of nearly identical radial size on top. Self-assembly of lipid molecules in bilayer structures is a fluid phenomenon, so the size of the layering bilayer can be tailored to fit the template by excising or adding more material from the stacking bilayers nearest neighbor. Subsequent bilayer stacking thus grows the columnar structure.

Figure 2:
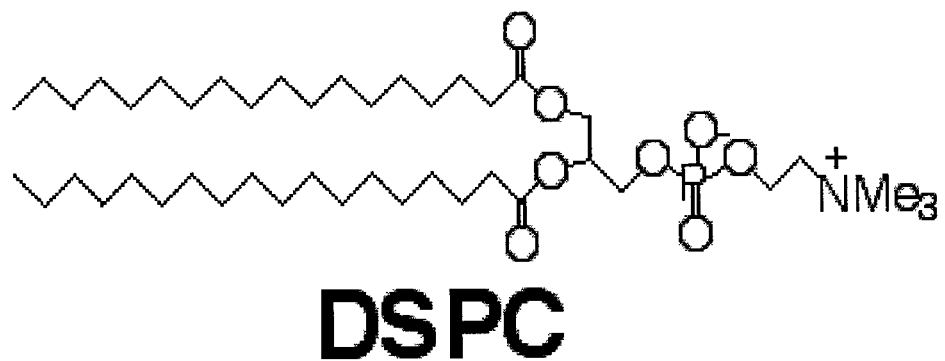
FIG. 2 shows a representation of the structure of DSPC and PSIDA.
Figure 2:
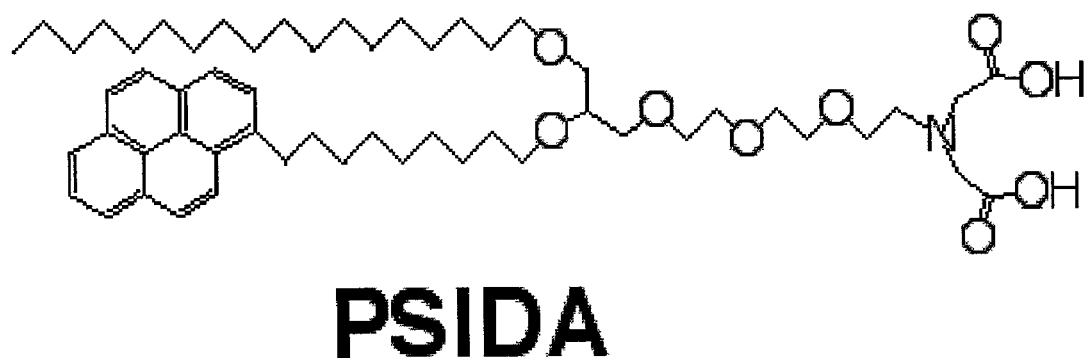

In one embodiment of this invention, $Cu^{2+}$ serves as the ligand and iminodiacetic acid as the receptor on the membrane surface. The receptor is expressed on a distearylphosphatidyl choline (DSPC) lipid membrane through a synthetically prepared molecule, PSIDA, 1-octadecyl-2-(9-(1-pyrene)nonyl)-rac-glycero-3-(8-(3,6-dioxy)octyl-1-amino-N,N-diacetic acid), at a 5 mole % loading. PSIDA is functionalized at the tail position with a pyrene and at the head position with iminodiacetic acid. FIG. 2 shows a representation of the structure of DSPC and PSIDA.

In accordance with the present invention, the lipid bilayer stacks are formed through a chemical recognition-induced self-assembly of lipid bilayer vesicles (liposomes). Recognition sites for ligands (e.g., metal ions) decorate the surface of the liposome at a low to moderate surface concentration (1–20 mole %). A schematic illustration of a lipid bilayer vesicle, composed of receptor and matrix lipids, spontaneously converting into a stacked bilayer column upon ligand addition is shown in FIG. 1. For the 5 mole % PSIDA/DSPC bilayers, PSIDA is the receptor lipid while DSPC serves as the matrix and $Cu^{2+}$ is the ligand. Liposomes of these lipids were prepared using probe sonication (Sasaki, D. Y.; Waggoner, T. A. Proc. SPIE-Int. Soc. Opt. Eng. 1999, 3606, 46–54). The bilayer structures were negatively stained using a standard TEM preparation protocol with ammonium molybdate. Transmission electron micrograph (TEM) images were taken on a Philips CM-30 operated at 300 kV, demonstrating that small unilamellar vesicles (SUV) of 5% PSIDA/DSPC bilayers are formed in MOPS buffered water (0.02 M MOPS, 0.10 M NaCl) at pH 7.4, with free-floating liposome structures observed. Liposome sizes ranged between 400–700 nm in diameter. In addition, various forms of unstructured bilayer aggregates were seen, accounting for approximately 50% of the observed features.

In previous work, liposomes composed of a pyrene-labeled synthetic receptor lipid (e.g., PSIDA) mixed into a DSPC matrix performed as highly selective optical sensors for heavy metal ions (Sasaki, D. Y.; Shnek, D. R.; Pack, D. W.; Arnold, F. H. Angew. Chem., Int. Ed. Engl. 1995, 34, 905; Sasaki, D. Y.; Padilla, B. E. Chem. Comm. 1998,1581; Sasaki, D. Y.; Waggoner, T. A. Proc. SPIE-Int. Soc. Opt. Eng. 1999, 3606, 46–54). In the absence of metal ions, the liquid-phase receptor lipid separates from the solid-phase DSPC matrix, producing fluorescence spectra with large excimer emission ($\lambda_{max}$=470 nm) and relatively small monomer emission ($\lambda_{max}$=375 nm). Addition of di- or trivalent metal ions causes an inversion of the fluorescence emission peaks (excimer emission attenuates as the monomer emission intensifies) revealing dispersion of the receptor lipids into the DSPC matrix upon the metal ion recognition. Complete reversibility of the process is possible by removal of metal ion with EDTA.

Addition of $Cu^{2+}$ to lipid bilayers composed of 5% PSIDA/DSPC (>0.1 mM lipid) caused the solution to become turbid, indicative of vesicle aggregation. The turbidity was, like the metal ion response, reversible upon the addition of EDTA. Turbid solutions were not observed with other receptor lipids that were selective for $Hg^{2+}$ or $Pb^{2+}$, nor with the 5% PSIDA/DSPC liposomes in the presence of other divalent metal ions, such as $Mn^{2+}$ or $Ca^{2+}$.

TEM images of the 5% PSIDA/DSPC with $Cu^{2+}$ solution found columnar structures of self-assembled stacks of lipid bilayers. Representative images are shown in Waggoner et al. (Waggoner, T. A; Last, J. A; Kotula, P. G.; Sasaki, D. Y. J. Am. Chem. Soc. 2001, 123, 496–497. Approximately 15–20% of the observed bilayer structures on the TEM grid were in the form of these columns and the process has been reproduced. These columnar structures varied in width ranging from 600 to 900 Å with lengths running anywhere between several (300 Å) to ~45 (3300 Å) bilayer thickness. The structure appears to be composed of individual lipid bilayers approximately 40 Å thick with approximately 30 Å spacing between each layer. It does not appear that these are flattened liposomes since the edges of each bilayer in the stack are discreet with no connectivity with its adjacent neighbor. The stacks have several common features. One end of the stack has a short, poorly organized stack of bilayers that is approximately half the diameter of the column. At the other end, the stacks tend to taper off in size in the final few bilayers.

The initial liposome size distribution is polydisperse, but the resultant self-assembled structure is well defined in width. From the fluorescence data, it is known that $Cu^{2+}$ binding to the iminodiacetic acid (IDA) receptor induces a dispersion of PSIDA molecules into the lipid matrix. Coordination of $Cu^{2+}$ to the IDA headgroup leaves open an equivalent coordination site for another IDA to bind. The fluorescence data also indicates that intra-liposome 2:1 coordination of IDA to $Cu^{2+}$ does not occur, most probably due to geometric constraints of the two-dimensional surface. Orientation of the $Cu^{2+}$-IDA complex perpendicular to the surface would, however, allow complexation with an IDA from another liposome. Through this metal ion-coordination-mediated event numerous adhesion points between the two liposomes would rapidly propagate resulting in a flattening of the opposing bilayers (FIG. 1). The dispersion of receptors, due to metal ion binding, should aid in the uniform adhesion over the area between the bilayer surfaces. At some point, the liposome ruptures as a result of deformation from the adhesion process allowing $Cu^{2+}$ to reach receptors in the liposome's interior. The bilayers can be considered to be in the shape of a disc, as one might think of a flattened sphere. The first one or two bilayers formed can serve as a template for successive stacking of bilayers regulating the width through the adhesion points between bilayers. The self-organizing nature of lipid assemblies can allow the bilayers to restructure, either recruiting or displacing lipids from adjacent bilayers to form a contiguous bilayer that matches the template.

The range of sizes observed with these structures, currently, is 600–900 Å in diameter and lengths spanning from 300 to 3300 Å or more. Widths are highly defined within each structure, exhibiting the self-limiting nature of the material's growth. Lengths, on the other hand, do not appear to have any self-limiting characteristics allowing possible growth to any length.

EXAMPLES

DSPC was obtained from Avanti Polar Lipids, Inc. and was used as received. PSIDA was prepared as described previously (Ng, K.; Pack, D. W.; Sasaki, D. Y.; Arnold, F. H. Langmuir 1995, 11, 4048. $CuCl_2$ (99.9999%) was obtained from Aldrich and used as received. All other compounds and solvents were of reagent grade from Fisher Scientific. All aqueous solutions were prepared from water purified through a Barnstead Type D4700 NANOpure Analytical Deionization System with ORGANICfree cartridge registering an 18.0 MΩ-cm resistance. TEM images were taken on a Philips CM-30 operated at 300kV. All samples were stained using ammonium molybdate.

A. Receptor Lipids

Lipids functionalized with receptor groups for specific ligands were prepared synthetically using known procedures, such as described by Arnold et al. (U.S. Pat. No. 5,837,202, issued on Nov. 17, 1998; incorporated herein by reference).

B. Lipid Bilayer Material Preparation

Stock solutions of distearylphosphatidylcholine (DSPC) and 1-octadecyl-2-(9-(1-pyrene)nonyl)-rac-glycero-3-(8-(3,6-dioxy)octyl-1-amino-N,N-diacetic acid) (PSIDA) were prepared by dissolving 159 mg of DSPC in 100 mL of chloroform to give a 2.02 mM solution and 5.65 mg of PSIDA in 10 mL of chloroform to give a 0.60 mM solution. From the stock solutions 5.00 mL of DSPC solution and 0.83 mL of PSIDA solution were transferred into a 15 mL capacity conical shaped tube. Solvent was removed under reduced pressure on a rotary evaporator at 40–45° C., to form a homogeneously thin lipid film. The films were further dried at room temperature under high vacuum (50 μmHg) overnight. To the tube was added 3.0 mL of freshly prepared 4-morpholinepropanesulfonic acid (MOPS) buffer solution (0.02 M MOPS, 0.10 M NaCl, pH 7.4). The solution was vortexed at 60–65° C. until the lipid film was completely suspended, degassed with $N_2$ gas for several minutes, then probe tip sonicated on an Ultrasonic Processor at 25 watts in an ice bath for ~40 minutes using a cycle of 3 minutes of sonication followed by 1 minute of resting. The solution was centrifuged for 30 minutes at 16,000 g (Fisher Micro 16 Centrifuge) and the supernatant was filtered through a 0.2 mm syringe filter. The clear liposome solution was then diluted with MOPS buffer to give a desired concentration.

C. Lipid Bilayer Stacks

To a solution of the 5% PSIDA/DSPC liposomes, at a total lipid concentration of 3 mM, was added $CuCl_2$ at a 1 μM concentration in a 0.10 M NaCl aqueous solution. The solution was swirled gently at room temperature for several seconds then let incubate at room temperature overnight.

D. TEM Sample Preparation

A TEM carbon-coated Cu grid was prepared in accordance with standard procedures. Specifically, the grid was pretreated with a drop of bacitracin (0.1 mg/mL aqueous) for one minute, then drawn off with a piece of filter paper. A drop of the liposome solution was then placed on the bacitracin-treated grid and let sit for one to two minutes before drawn off with a piece of filter paper. Immediately after, a drop of 1% aqueous ammonium molybdate was placed on top of the grid and let sit for one minute, then drawn away with filter paper. The sample was let dry for several hours before imaging with a Philips CM-30 operated at 300 kV.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A self-assembled lipid bilayer material comprising a plurality of lipid bilayer molecules, each lipid bilayer molecule layered upon another lipid bilayer molecule, in a stacked columnar structure of less than a maximum of 900 Angstroms in diameter.

2. The self-assembled lipid bilayer material of claim 1 wherein each lipid bilayer molecule in said stacked columnar structure has a diameters in the range between approximately 600 Angstroms and approximately 900 Angstroms.

3. The self-assembled lipid bilayer material of claim 1 wherein the columnar structure is greater than approximately 300 Angstroms in length.

4. The self-assembled lipid bilayer material of claim 1 wherein the material is stable is aqueous solutions.

5. The self-assembled lipid bilayer material of claim 1 wherein a ligand is intercalated between said lipid bilayer molecules.

6. The self-assembled lipid bilayer material of claim 5 wherein said ligand has at least two bindings sites accessible from opposite sides of the ligand.

7. The self-assembled lipid bilayer material of claim 5 wherein said ligand is a cation.

8. The self-assembled lipid bilayer material of claim 5 wherein said ligand is a copper cation.

9. The self-assembled lipid bilayer material of claim 1 wherein said lipid bilayer molecules are functionalized with a receptor molecule.

10. The self-assembled lipid bilayer material of claim 9 wherein said receptor molecule is iminodiacetic acid.

11. The self-assembled lipid bilayer material of claim 1 wherein molecules selected from proteins, polymers and metal oxides are intercalated between said lipid bilayer molecules.

* * * * *